United States Patent [19]

Lamson et al.

[11] 4,049,736
[45] Sept. 20, 1977

[54] DEHYDRATION OF α-METHYLBENZYL ALCOHOLS TO FORM MONOVINYLIDENE AROMATIC MONOMERS

[75] Inventors: Junior J. Lamson, Bay City; Richard H. Hall, Midland; Edward Stroiwas, Merrill; Larry D. Yats, Midland, all of Mich.

[73] Assignee: The Dow Chemical Company, Midland, Mich.

[21] Appl. No.: 601,946

[22] Filed: Aug. 4, 1975

Related U.S. Application Data

[63] Continuation-in-part of Ser. No. 39,889, May 22, 1970, abandoned.

[51] Int. Cl.² .................... C07C 15/00; C07C 15/10
[52] U.S. Cl. ...................... 260/669 QZ; 260/650 R
[58] Field of Search ............... 260/669 QZ, 650 R

[56] References Cited

U.S. PATENT DOCUMENTS

| 2,399,395 | 4/1946 | Shriver | 260/669 QZ |
| 2,407,291 | 9/1946 | Quattlebaum et al. | 260/669 QZ |
| 2,482,207 | 9/1949 | Quattlebaum et al. | 260/669 QZ |
| 2,482,208 | 9/1949 | Quattlebaum et al. | 260/669 QZ |
| 3,658,928 | 4/1972 | Skinner | 260/669 QZ |

Primary Examiner—O. R. Vertiz
Assistant Examiner—Eugene T. Wheelock
Attorney, Agent, or Firm—M. S. Jenkins

[57] ABSTRACT

α-Alkylbenzyl alcohol and substituted α-alkylbenzyl alcohols are converted in high yield and purity to styrene and substituted styrenes by contacting the alcohol in vapor phase with silica gel and steam.

12 Claims, No Drawings

DEHYDRATION OF α-METHYLBENZYL ALCOHOLS TO FORM MONOVINYLIDENE AROMATIC MONOMERS

CROSS-REFERENCE TO RELATED APPLICATION

The present application is a continuation-in-part of our previous application Ser. No. 39,889 filed May 22, 1970 now abandoned.

BACKGROUND OF THE INVENTION

This invention relates to the vapor phase dehydration of α-alkylbenzyl alcohols and sustituted analogues thereof to form styrene and substituted styrenes.

Dehydration of alcohols to their corresponding unsaturated structural compounds is well known in the art. Dehydration techniques are not generally employed in the manufacture of styrene and many homologues thereof because standard dehydrogenation of ethyl benzene is considered to be a more economic route. In addition, styrenes produced by conventional dehydration techniques often contain enough ethyl benzene and other impurities to require extensive purification.

It is characteristic of standard dehydrogenation techniques employed in the production of styrene that fairly large quantities of unreacted ethyl benzene be present in the styrene fraction. Such quantities of ethyl benzene in the styrene fraction are substantial enough to cause loss of properties in polymers of such styrene fractions. Furthermore, due to the closeness of the boiling points of styrene and ethyl benzene, removal of ethyl benzene by distillation is expensive.

Moreover, normal dehydrogenation of many substituted ethyl benzenes, particularly the tertiary alkyl substituted ethyl benzenes, destroys or alters the substituted group. For example, dehydrogenation of ar-(t-alkyl)-ethyl benzene to form their corresponding styrenes usually results in rupture and/or loss of the t-alkyl group as well as ethyl group dehydrogenation.

Attempts to prepare ar-(t-alkyl)styrenes by conventional dehydration of the corresponding ar-(t-alkyl)-α-methylbenzyl alcohols have not been satisfactory due to the formation of other byproducts and the rupture of the t-alkyl group which frequently accompanies dehydration. As a result of this rupture, appreciable quantities of ethyl benzene and under certain conditions, diolefinically unsaturated aromatic monomers are formed in addition to the desired ar-(t-alkyl)styrene. These diolefinically unsaturated aromatic monomers, e.g., ar-(i-propenyl)styrene in dehydration of ar-(t-butyl)-α-methylbenzyl alcohol, are very difficult to separate from the desired ar-(t-alkyl)styrene. During polymerization of the ar-(t-alkyl)styrene monomer, the diolefinically unsaturated aromatic monomer acts as a crosslinking agent thereby producing a substantially crosslinked styrene polymer which is insoluble in many organic solvents such as toluene and benzene. This lack of solubility is undesirable in many applications employing such styrene polymers.

Conventional dehydration techniques for preparing styrene and substituted styrenes are not completely satisfactory in that substantial amounts of ethyl benzene and other difficult to separate impurities often remain or are produced. Such difficulties have been pointed out in prior publications such as U.S. Pat. Nos. 2,399,395 and 3,442,963.

Therefore, it would be highly desirable to provide a new, improved technique for producing styrene and substituted styrenes in high yield which contain little or no ethyl benzene and other impurities, particularly diolefinicially unsaturated aromatic monomers.

SUMMARY OF THE INVENTION

Accordingly the present invention is an improved process for dehydrating α-alkylbenzyl alcohols and to form the corresponding styrene monomer in high yield and purity. This improved process comprises contacting an α-alkylbenzyl alcohol, as hereinafter described in detail, in vapor phase with a silica gel dehydration catalyst in the presence of from about 0.03 to about 25 parts by weight of added water per part by weight of alcohol.

Prior art teachings indicate that water produced during dehydration of an alcohol should be removed from the reaction mixture in order to move the reversible dehydration reaction to the right and thereby increase the yield of the unsaturated product. Surprisingly in the process of this invention wherein silica gel is employed as the dehydration catalyst, it is found that presence of water, preferably accomplished by addition of from about 0.03 to about 25 parts by weight per part of alcohol to the alcohol prior to dehydration and/or during dehydration, effectively increases the yield of the desired styrene and substantially reduces, and under optimum conditions, almost completely eliminates the formation of ethyl benzene and other impurities which are difficult to separate. In general, the desired monovinylidene aromatic monomer is produced in purity greater than about 99 mole percent and contains less than about 0.5 mole percent of alkyl benzene impurity, so-called ethyl benzene impurity.

As a result, styrene monomers produced by this method require little or no further purification to remove impurities having boiling points nearly the same as the monomer; thus expensive distillation procedures are eliminated. Styrene polymers produced from these styrene monomers are found to have improved properties as a result of the increased purity. As a result of low concentrations, i.e., less than 0.02 mole percent based on total monomer, of diolefinic impurity, ar-(t-alkyl)styrenes produced by this process can be polymerized directly into polymers which are soluble in toluene, benzene and other organic solvents. Such organic soluble polymers are particularly useful in various coatings, thermoplastic molding, reactive diluents, polyester varnish and chemical applications that require a monomer essentially free of diolefinic species.

DESCRIPTION OF THE PREFERRED EMBODIMENTS

For the purposes of this invention, the term "α-alkylbenzyl alcohol" includes α-alkylbenzyl alcohols, especially a-methylbenzyl alcohol and substituted analogues thereof. Such alcohols are represented by the general formula:

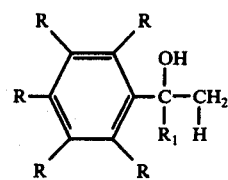

wherein R is hydrogen, alkyl having from 1 to 12 carbon atoms, e.g., methyl, t-butyl, t-amyl and other t-alkyl; halogen, e.g., bromo, chloro, and fluoro; or the like and $R_1$ is hydrogen or alkyl having from 1 to 4 carbon atoms.

Exemplary α-alkylbenzyl alcohols include α-methylbenzyl alcohol, ar-chloro-α-methylbenzyl alcohol, ar-bromo-α-methylbenzyl alcohol, ar-fluoro-α-methylbenzyl alcohol, ar-dichloro-α-methylbenzyl alcohol, ar-dibromo-ar-chloro-α-methylbenzyl alcohol, ar-chloro-α-ethylbenzyl alcohol, 4-chloro-2,5-difluoro-α-methylbenzyl alcohol, ar-(t-butyl)-α-methylbenzyl alcohol, ar-(t-amyl)-α-methylbenzyl alcohol, ar,α-dimethylbenzyl alcohol, α-ethyl-2-isopropyl-5-methylbenzyl alcohol, α-isobutyl-2,4,5-trimethylbenzyl alcohol, and the like.

Preferred α-alkyl benzyl alcohols are amethyl-benzyl alcohol, ar-halo-α-methylbenzyl alcohol such as ar-chloro- and ar-bromoα-methylbenzyl alcohol and ar-(t-alkyl)α-methylbenzyl alcohols such as p-(t-butyl)α-methylbenzyl alcohol, p-(t-amyl)-α-methylbenzyl alcohol and similar alcohols wherein t-alkyl has 4 to 8 carbon atoms. The above alcohols are known compounds and can be prepared by syntheses obvious to those skilled in the art. Illustratively, ar-alkyl-α-methylbenzyl alcohols can be prepared by the stepwise synthesis of (1) alkylating ethyl benzene with olefin in the presence of sulfuric acid in accordance with the method of Ipatieff et al., *JACS*, Vol. 58, 919(1936), (2) oxidizing the alkylated ethyl benzene to the corresponding acetophenone-alcohol mixture as described by H. J. Sanders et al., *I & E Chem*, Vol 45, 2 (1953), and (3) reducing the mixture by catalytic hydrogenation to the desired alcohol.

Silica gel dehydration catalyst employed in this invention may be in any of the several forms of silica gel which will permit intimate contact between the silica gel and alcohol vapor during the dehydration. It is desirable that the silica gel be in the form of a divided solid, preferably in the form of particles not measuring more than about an inch in any dimension. Further the silica gel should be of a type that is not degraded or destroyed when contacted with large quantities of water. Although good results are obtained with a number of grades of particulate silica gel, best results are obtained with the silica gel in the form of a particulate solid having a mesh size ranging from about 2 to about 400 and a surface area of at least about 300 square meters per gram, preferably from 300 to 900 m²/g. In these preferred embodiments, the possibility of complete contact between the silica gel and the alcohol is maximized. It is especially preferred that the silica gel be finely divided porous particles having an average pore diameter ranging from about 2 to about 200 Angstrom Units. Methods for preparing silica gel are well known to skilled artisans. Also any of several commercial grades of silica gel fitting the above general description may be employed.

It is to be understood that the silica gel may be employed in combination with other materials such as binders, fillers and commonly employed inert supporting materials such as fused alumina, crushed sandstone, and silica, filter stone and ceramically bonded silica.

In the practice of this invention the α-alkylbenzyl alcohol in vapor phase is contacted with the silica gel in the presence of from about 0.03 to about 25 parts by weight of water per part by weight of alcohol, preferably from about 0.5 to about 20 weight parts, especially from about 1 to about 2 parts of water per weight part of alcohol. It is generally preferable that the alcohol be intimately mixed with specified amounts of water in the form of steam prior to dehydration. This is easily accomplished by passing liquid or vaporous mixtures of the alcohol and water over or through a bed or column of an effective heat transfer material such as silicon carbide, fused ceramic packing or non-corrosive metal packing. In such embodiments, a column having a lower portion of a bed of catalytic silica gel and an upper portion of the heat transfer agent can be made and the alcohol containing water is then passed downward into the column through the heat transfer agent and then through the catalytic silica gel bed. It is often desired to employ an organic carrier liquid which is a solvent for the alcohol, e.g., toluene or benzene, but which can be easily removed by simple distillation. In such embodiments, the alcohol and carrier liquid are mixed together prior to vaporization of the alcohol mixture. It is understood addition of water to the reaction may be made after the alcohol has passed through the heat transfer agent. Also the water need not be added in the form of steam or super-heated steam although it is preferred to do so.

Generally, the desirable temperatures of operation of the process of this invention are in the range of about 200° to 510° C, preferably from about 260° to about 450° C, especially from about 300° to about 400° C. In the dehydration of ar-(t-alkyl)-α-methylbenzyl alcohols, it is desirable to employ dehydration temperatures above 260° C, preferably about 325° to about 425° C, in order to insure contact between the dehydration catalyst and the alcohol in the vapor state. It is generally desirable to carry out dehydration at atmospheric pressure, although it is possible to achieve dehydration with relatively good purity and yield at subatmospheric to superatmospheric pressure, e.g., from about 0.2 to about 5 atmospheres. Vaporization of the alcohol, however, may be advantageously achieved by using reduced pressure. Vaporization may also be achieved by contacting the alcohol with steam or superheated steam substantially prior to dehydration.

The quantity of silica gel which effectively dehydrates the alcohol depends in part upon the rate at which the vaporous alcohol is to be passed through the silica gel bed or column, upon the surface area of the gel per unit of weight, upon the amount of water to be employed. Generally higher vapor flow rates and larger quantities of water require more silica gel to achieve effective dehydration.

Practice of the present invention as described hereinbefore yields the desired monovinylidene aromatic monomer, particularly the ar-(t-alkyl)styrene, in purity greater than 99 mole percent based on total product after simple distillation which removes unreacted ketones and alcohols. Accordingly, the alkyl benzene impurity is held below 0.5 mole percent. In the dehydration of the ar-(t-alkyl)-α-methylbenzyl alcohols by the method of this invention, diolefinic and other polyolefinic impurity is held below 0.02 mole percent based on total product after simple distillation.

The invention is further illustrated by the following examples which should not be construed as limiting the scope of the invention. All parts and percentages are by weight unless otherwise indicated.

EXAMPLE 1

A mixture of 50 parts of α-methylbenzyl alcohol and 50 parts of toluene is preheated to 300° C and mixed with 100 parts of steam at 300° C. The mixture is passed downward through a glass column (1 inch outside diameter × 27 inch length) equipped with an electric furnace and containing a 14-inch upper layer of silicon carbide (8 mesh) preheated to 350° C and a 6-inch lower layer (20 g) of silica gel (on 10 mesh, 300 m² of surface area/g). Water and dehydrated organic product are condensed in the lower part of the column, collected and separated. The organic product is dried and distilled. The distilled product is determined by infrared spectroscopy and vapor phase chromatography to be 99+ mole percent styrene containing less than 0.5 mole percent of ethyl benzene. Overall yield on the basis of starting alcohol is greater than 95 percent.

EXAMPLE 2

A mixture of 50 parts of 4-(t-butyl)-α-methylbenzyl alcohol and 50 parts of toluene is prepared. A reaction column (1 inch outside diameter × 27 inch length) is filled to a bed height of 8–9 inches with silica gel (8–10 mesh, 340 m² of surface area/g, 140A average pore diameter) and sufficient amount of silicon carbide (6 mesh) is added to the tube to increase total bed height to 16 inches. The reaction column is heated to 300° C. Water preheated to 300° C and the mixture are added simultaneously into the feed end of the column at rates of 90 ml/hr and 45 ml/hr respectively. An intimate admixture of steam and the alcohol mixture in vapor phase is formed and passes downward through the silicon carbide preheated to 350° C which acts as a preheat section for the vapor and then through the silica gel to effect dehydration. Following passage through the silica gel, water and organic product are condensed in the column, and collected. The dehydrated organic product is decanted, dried and distilled. The distilled product is determined by infrared spectroscopy and vapor phase chromatography to be 4-(t-butyl)styrene at 99 percent or greater purity. Overall yield on basis of amount of starting alcohol is greater than 90 percent.

Polymerization of the 4-(t-butyl)styrene by heating in the presence of benzoyl peroxide yields a polymer which is soluble in toluene at 20° C.

EXAMPLE 3

Several sample runs are carried out generally according to the procedure of Example 2. In these runs, mixtures of 50 parts of 4-(t-butyl)-α-methylbenzyl alcohol and 50 parts of toluene are prepared and mixed with varying amounts of steam. The vaporous steam-alcohol mixture is passed downward into a glass column (1 inch OD × 27 inch length) having a 14 inch upper bed of silicon carbide (10 mesh) preheated to varying temperatures and a 6 inch lower bed of silica gel (same as in Example 2). Water and dehydrated organic product are condensed, collected and separated as in Example 2. The results are recorded in Table I.

To show the particular advantage of employing added water in this system, a control run ($C_1$) is made under conditions similar to the above runs with the exception that no water is added to the alcohol at any point prior to or during dehydration, the results of this control run are also recorded in Table I. To indicate upper limits as to temperature during dehydration, two control runs ($C_2$ and $C_3$) employing varying amounts of water are also carried out in accordance with the procedures employed in the above sample runs. The results are recorded in Table I.

TABLE I

| Sample Run No. | Water/Alcohol parts per part | Reaction Temperature (1), ° C | Impurities (2) Isopropenyl Styrene, mole % | 4-(t-Butyl)Ethyl Benzene, mole % | Polymer (3) Solubility |
|---|---|---|---|---|---|
| 1 | ~5.0 | 410 | 0 | 0.15 | Soluble |
| 2 | ~1.4 | 406 | 0 | 0.15 | Soluble |
| 3 | ~0.84 | 406 | 0 | 0.14 | Soluble |
| 4 | ~0.56 | 395 | 0 | 0.13 | Soluble |
| 5 | ~20.0 | 393 | 0 | 0.2 | Soluble |
| 6 | ~20.0 | 445 | 0 | 0.2 | Soluble |
| 7 | ~20.0 | 505 | <0.02 | 0.7 | Soluble |
| 8 | ~0.50 | 400 | 0 | 0.1 | Soluble |
| 9 | ~0.50 | 448 | 0 | 0.4 | Soluble |
| 10 | ~0.50 | 506 | <0.02 | 0.6 | Soluble |
| $C_1$* | ~0 | 400 | 0.12 | 0.23 | Insoluble |
| $C_2$* | ~20.0 | 550 | >0.11 | 1.4 | Insoluble |
| $C_3$* | ~0.50 | 550 | >0.18 | 1.5 | Insoluble |

*Not an example of the invention
(1) Reaction temperature corresponds to temperature of silicon carbide heat transfer means.
(2) Approximate mole % of the specified impurity based on moles of p-(t-butyl)styrene produced. Determined by Gas Phase Chromatography and infrared Spectroscopy.
(3) Solubility of 10% p-(t-butyl)styrene polymer in toluene at 23° C.

EXAMPLE 4

Several sample runs are carried out essentially according to Example 2 except that a wide range of temperatures are employed. In the several runs, mixtures of 50 parts of ar-(t-butyl)-α-methylbenzyl alcohol containing ~7 mole percent of ar-(t-butyl)acetophenone and 50 parts of toluene are prepared. A glass column (1 inch OD and 16 inch length) equipped with an electric furnace is filled to a height of 3.5 inches with silicon carbide (8 mesh, 42 grams), to a total height of 13.5 inches with silica gel (same as in Example 2, 50 grams), and to total height of 16.0 inches with silicon carbide (8 mesh, 40 grams) and preheated to varying temperatures from 200° to 500° C for the several runs. Steam superheated to at least 550° C and the alcohol/toluene mixture are added simultaneously into the feed end of the column at rates of 100 ml/hour (measured as condensed water) and 50 ml/hour respectively. An intimate admixture of steam and the alcohol mixture in vapor phase is formed and passes downward through the heat transfer agent and the silica gel to effect dehydration. The water and organic product are then condensed, collected and separated. The organic product is distilled and dried, and its constituency is determined by infrared spectroscopy and vapor phase chromatography. The results are shown in Table II.

To point out the advantage of silica gel catalysts over conventional dehydration catalyst, several control runs ($C_4$–$C_8$) are made employing essentially the same procedure used above except that a titania dehydration catalyst (4–8 mesh, and 170 m²g of surface area/g) is substituted for silica gel. The dehydration column has a 3.5 inch bottom layer of silicon carbide (8 mesh), a 10 inch middle layer of titania catalyst and a 2.5 inch top layer of silicon carbide. The organic product is recovered and analyzed by infrared spectroscopy and vapor phase chromatography and the results are recorded in Table II.

ency is determined by the means described above. The results are also recorded in Table III.

TABLE III

| | | Product Constituency, mole percent | | | | |
|---|---|---|---|---|---|---|
| Sample Run No. | Catalyst | p-(t-butyl)-styrene | m-(t-butyl)-styrene | ar-(t-butyl) ethylbenzene | ar-(t-butyl)toluene and ar-(t-butyl)benzene | ar-(t-butyl)acetophenone ar-(t-butyl)-α-methyl-benzyl alcohol, ppm |
| 1 | Silica Gel | 96.09 | 3.77 | 0.10 | 0.04 | <25 ppm |
| $C_9$* | Alumina | 96.52 | 2.32 | 1.08 | 0.08 | ~45 ppm |

*Not an example of the Invention

TABLE II

| Sample Run No. | Reaction Temperature, °C | Catalyst | Product Constituency, mole % | | | |
|---|---|---|---|---|---|---|
| | | | ar-(t-butyl)-styrene | ar-(t-butyl)-ethyl benzene | ar-(t-butyl)-acetophenone | ar-(t-butyl)-α-methyl-benzyl alcohol |
| 1 | 250° | Silica Gel | 92.1 | 0.5 | 4.4 | 3.0 |
| 2 | 300° | Silica Gel | 95.3 | 0.3 | 4.5 | — |
| 3 | 350° | Silica Gel | 95.9 | 0.3 | 3.9 | — |
| 4 | 400° | Silica Gel | 97.2 | 0.2 | 2.6 | — |
| 5 | 450° | Silica Gel | 95.3 | 0.2 | 4.5 | — |
| 6 | 500° | Silica Gel | 94.2 | 0.5 | 5.3 | — |
| $C_4$* | 250° | Anhydrous Titania | 97.3 | 0.4 | 2.3 | — |
| $C_5$* | 300° | Anhydrous Titania | 97.2 | 0.6 | 2.2 | — |
| $C_6$* | 350° | Anhydrous Titania | 94.1 | 1.9 | 4.0 | — |
| $C_7$* | 400° | Anhydrous Titania | 91.9 | 5.4 | 2.7 | — |
| $C_8$* | 450° | Anhydrous Titania | 83.5 | 12.3 | 3.3 | — |

*Not an example of the Invention

As evidenced by Table II, significantly larger quantities of ar-(t-butyl)-ethyl benzene are generally produced in dehydration employing titania as catalyst than those employing silica gel under essentially the same conditions. The ar-(t-butyl)-ethyl benzene is difficult to separate from ar-(t-butyl)styrene whereas ar-(t-butyl)acetophenone is separated from either of the above by simple distillation.

EXAMPLE 5

A solution of 50 parts of ar-(t-butyl)-α-methylbenzyl alcohol containing ~7 mole percent of ar-(t-butyl)acetophenone in 50 parts of toluene is mixed with superheated steam (550° C) in a ratio of 2 parts of water to one part of the mixture. The steam-alcohol mixture is passed downward through a glass column (1 inch OD × 21 inch length) containing a 10 inch upper layer of silicon carbide and a 10 inch lower layer of silica gel (same as in Example 2). The temperature at the top of the column is 350° C and at the bottom of the column is 325° C. The water and organic product is distilled and dried, and its constituency is determined by infrared spectroscopy and vapor phase chromatography. The results are shown in Table III.

For the purpose of comparison a control run ($C_9$) is carried out by following the above process except that alumina (4–8 mesh and 210 m²g of surface area/gram) is substituted for silica gel as a dehydration catalyst. The organic product is distilled and dried and its constitu-

EXAMPLE 6

The dehydration process of the present invention is carried out in a continuous manner by continuously feeding molten ar-(t-buty)-α-methylbenzyl alcohol at 200 lb/hr and water superheated to 550° C at 400 lb/hr into a column (18 inch OD × 6 foot 8 inch length). The column contains a 3 foot 4 inch upper bed of metallic heat transfer material preheated to 350° C and a 3 foot 4 inch lower bed of silica gel (8–10 mesh, 340 m²/g, 140A average pore diameter). The temperature at the lower end of the column is 325° C. The dehydrated organic product is continuously collected at the lower end of the column and then recovered at 99+ percent purity by simple distillation. The dehydrated product is determined by infrared spectroscopy to be ar-(t-butyl)styrene.

EXAMPLE 7

Several samples of ar-chloro-α-methylbenzyl alcohol containing small amounts of ar-chloro-acetophenone are continuously dehydrated by mixing the liquid alcohol with varying amounts of superheated steam (550° C) and passed as vapor phase through the column described in Example 3. Dehydration temperatures for the various runs are also varied. The amounts of low boiling components are shown in Table IV.

For the purposes of comparison, similar samples of ar-chloro-α-methylstyrene also containing small amounts of ar-chloro-acetophenone are continuously dehydrated in the same manner except that no water is added during the process. The amounts of low boiling components for these control runs ($C_{10}$, $C_{11}$, $C_{12}$) are also shown in Table IV.

TABLE IV

| Sample Run No. | Water/Alcohol, ml/100 ml | Reaction Temperature, °C | Low Boiling Components of Reaction Mixture, parts (1) | | | Low Boiling Impurities/ ar-chlorostyrene, parts/100 parts |
| --- | --- | --- | --- | --- | --- | --- |
| | | | ar-chloro-styrene | ar-chloro-ethylbenzene | other | |
| 1 | 3 | 400 | 62.89 | 1.10 | 0.22 | ~2.1 |
| 2 | 5 | 400 | 76.19 | 0.88 | 0.19 | ~1.4 |
| C*10 | 0 | 400 | 55.80 | 1.88 | 0.45 | ~4.2 |
| 3 | 25 | 350 | 73.91 | 0.16 | 0.09 | ~0.34 |
| C*11 | 0 | 350 | 58.90 | 0.89 | 0.27 | ~1.80 |
| 5 | 50 | 400 | 78.11 | 0.03 | ND** | ~0.04 |
| C*12 | 0 | 400 | 63.64 | 1.61 | 0.45 | ~3.23 |

*Not an example of the invention
**None Detected
(1) Higher Boiling Components including chloroacetophenone and ar-chloro-α-methylbenzyl alcohol comprise the remaining reaction mixture having a total of 100 parts.

EXAMPLES 8–13

In accordance with the continuous dehydration process of Example 3, several substituted α-methylbenzyl alcohols are dehydrated to the corresponding substituted styrenes thereof. The results obtained are comparable to those obtained in Example 3. The alcohols successfully dehydrated are as follows:

ar-t-butyl-α,α-dimethylbenzyl alcohol
ar-dichloro-α-methylbenzyl alcohol
ar-dibromo-α-methylbenzyl alcohol
ar-di-t-butyl-α-methylbenzyl alcohol
ar-(1-ethyl-1-methylpentyl)-α-methylbenzyl alcohol
ar-t-butyl-ar-melthyl-α-methylbenzyl alcohol.

Several dehydration runs are also carried out using silica gel catalysts having different mesh sizes in the range from about 2 to about 400 and surface areas in the range from about 300 to about 900 m²/g with good results.

What is claimed is:

1. A process for preparing an ar-(t-alkyl)styrene by dehydrating an α-alkylbenzyl alcohol represented by the general formula

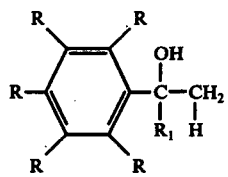

wherein each R is independently hydrogen, alkyl having from 1 to 12 carbon atoms or halogen provided that an R group is t-alkyl and $R_1$ is hydrogen or alkyl having 1 to 4 carbon atoms which method comprises a dehydration step of contacting the α-alkylbenzyl alcohol in vapor phase with a silica gel dehydration catalyst consisting essentially of silica gel in the presence of from about 0.03 to about 25 parts by weight of added water per part by weight of alcohol, said dehydration step being carried out at temperatures above 260° up to about 510° C, and subsequent simple distillation step of distilling the dehydration product to obtain the ar-(t-alkyl)styrene in purity greater than about 99 mole percent and containing less than 0.02 mole percent of diolefinic impurity.

2. The process according to claim 1 wherein the water in the form of steam is mixed with the α-alkylbenzyl alcohol prior to contacting the alcohol with silica gel.

3. The process according to claim 1 wherein the silica gel is in the form of a divided solid having a surface area of at least about 300 square meters/gram.

4. The process according to claim 3 wherein the silica gel is divided, porous solid having an average pore diameter ranging from about 2 to about 200 Angstrom units.

5. the process according to claim 1 wherein the alcohol is ar-chloro-ar-(t-butyl)-α-methylbenzyl alcohol.

6. The process according to claim 1 wherein the alcohol is ar-bromo-ar-(t-alkyl)-α-methylbenzyl alcohol.

7. The process according to claim 1 wherein the alcohol is an ar-(t-butyl)-α-methylbenzyl alcohol.

8. The process according to claim 7 wherein the t-alkyl is t-butyl.

9. The process according to claim 7 wherein the t-alkyl is t-amyl.

10. A continuous process for preparing ar-(t-alkyl)styrene which comprises (1) passing a vapor phase of an ar-(t-alkyl)-α-methylbenzyl alcohol and from about 0.5 to about 20 parts by weight of water in the form of superheated steam per part of the alcohol through a column containing a heat transfer agent and a silica gel dehydration catalyst consisting essentially of silica gel in the form of a divided solid having a surface area of at least 300 square meters per gram, said process being carried out at a dehydration temperature from about 260° to about 425° C such that the alcohol is dehydrated, and (2) recovering by simple distillation the resulting dehydration product in the form of ar-(t-alkyl)styrene of purity greater than about 99 mole percent and containing less than 0.02 mole percent of diolefinic impurity.

11. The process of claim 1 wherein the alcohol is ar-(t-butyl)-α-methylbenzyl alcohol consisting essentially of the meta and para isomers thereof, from about 0.5 to about 20 parts by weight of water per part of alcohol are employed and the temperature is within the range from 390° to 505° C.

12. The process of claim 10 wherein the dehydration temperature is in the range from about 325° to about 425° C.